United States Patent [19]
Liersch et al.

[11] 3,962,036
[45] June 8, 1976

[54] PROCESS FOR THE MANUFACTURE OF 7-AMINO-CEPHALOSPORANIC ACID-TYPE COMPOUNDS

[75] Inventors: Manfred Liersch, Riehen; Jakob Nuesch, Arlesheim, both of Switzerland

[73] Assignee: Ciba-Geigy Corporation, Ardsley, N.Y.

[22] Filed: Dec. 6, 1974

[21] Appl. No.: 530,116

[30] Foreign Application Priority Data
Dec. 20, 1973 Switzerland.................... 17902/73

[52] U.S. Cl. .................................. 195/29; 195/36 P
[51] Int. Cl.² .................................. C12D 13/06
[58] Field of Search ............... 195/80 R, 36 P, 29

[56] References Cited
UNITED STATES PATENTS
3,801,464  4/1974  Gorman et al..................... 195/80 R
3,880,713  4/1975  Fleming et al..................... 195/36 P

*Primary Examiner*—A. Louis Monacell
*Assistant Examiner*—Robert J. Warden
*Attorney, Agent, or Firm*—Joseph G. Kolodny; John J. Maitner; Theodore O. Groeger

[57] ABSTRACT

In compounds of formula

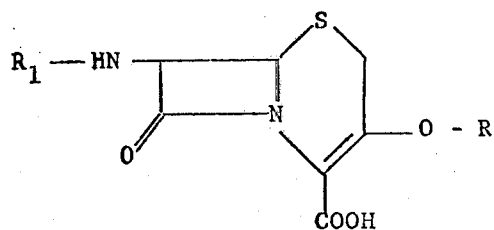

wherein R represents a lower alkyl radical and $R_1$ the acyl radical of a carboxylic acid the acylamino group is deacylated to the amino group when the compounds are treated with microorganisms possessing acylase activity or with extracts containing acylase or with the acylases themselves in aqueous medium. The isolation of the amino compounds so formed is carried out in known manner.

4 Claims, No Drawings

PROCESS FOR THE MANUFACTURE OF 7-AMINO-CEPHALOSPORANIC ACID-TYPE COMPOUNDS

The invention provides a novel process for the manufacture of amino compounds of the formula I

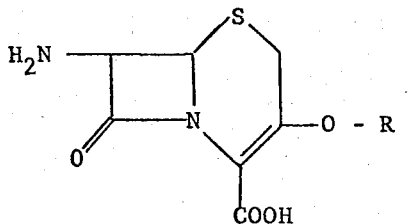

wherein R represents a lower alkyl radical, for example an ethyl, isopropyl, n-propyl or a tert. butyl radical, in particular a methyl radical. The compounds are useful starting products for the manufacture of therapeutically useful compounds, especially of corresponding N-acyl derivatives of the kind described, for example, in South African Patent 73/4050, for example 7-(D-α-amino-α-phenylacetamido)-3-methoxy-ceph-3-em-4-carboxylic acid.

The process according to the invention consists in treating compounds of the formula II

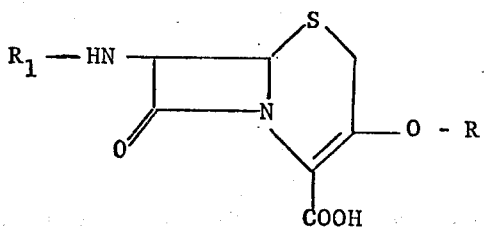

wherein R has the meaning previously assigned to it and $R_1$ represents the acyl radical of a carboxylic acid, with microorganisms possessing acylase activity or with extracts containing acylase or with the acylases themselves, in aqueous medium and isolating the compounds of the formula I from the solution.

In the compounds of the formula II, $R_1$ represents above all the acyl radical of a monovalent or divalent carboxylic acid of aliphatic character, for example of an aliphatic, cycloaliphatic, araliphatic or heterocyclylaliphatic carboxylic acid, in particular the acyl radical of lower alkane or lower alkene acids the alkyl or alkenyl radical of which can also be interrupted by oxygen or sulphur, or aryl-, aryloxy- or arylthio-lower alkane acids, wherein aryl represents in particular phenyl or, for example, phenyl which is substituted by hydroxy, lower alkyl or lower alkoxy, and the lower alkane acid is in particular acetic acid. Primarily, $R_1$ represents the acyl radical of naturally occuring penicillins, for example the radical of heptanecarboxylic, hexanecarboxylic or pentanecarboxylic acid, of pentane-2-carboxylic acid, butylthioacetic acid, allylthioacetic acid, phenylthioacetic acid, p-hydroxyphenylacetic acid and in particular of phenylacetic acid and phenyloxyacetic acid.

It is therefore preferable to use compounds of the formula II as starting materials, wherein R represents methyl, $R_1$ represents hydrogen and $R_2$ represents phenylacetyl or phenoxyacetyl.

Microorganisms possessing acylase activity and the extracts obtainable therefrom or more or less purified acylases as well as the methods for determining the acylase activity and the obtaining of acylases are known. They are dealt with, for example, in "Cephalosporins and Penicillins" by E. H. Flynn, Academic Press, New York and London, 1972, pp. 29–37 and 421–22 or in the publications of M. Cole, Process Biochemistry, 1967, pp. 35–46 and by Nüesch et al., Pathol. Microbiol. 30, 880 (1967). As is known, there are two types of acylases, namely those of bacterial origin (bacteria and Nocardia) which very rapidly deacylate Penicillin G but not Penicillin V, and those obtained from fungi, for example penicillium or cephalosporium (including yeasts and streptomycetes) which deacylate Penicillin V more rapidly than Penicillin G. In analogous manner, it is possible to use these acylases for deacylating compounds of the formula II with corresponding acyl radicals $R_1$. Possible microorganisms of acylase content which are suitable above all for the deacylation of compounds with the acyl radical of Penicillin G, namely the phenylacetyl radical, are primarily: *Escherichia coli, Bacillus subtilis, Bacillus megatherium,* also *Micrococcus roseus, Micrococcus lysodeikticus, Alcaligenes faecalis, Aerobacter cloacae* and Nocardia and those which are suitable for the deacylation of compounds with the acyl radical of Penicillin V, i.e. the phenyloxyacetyl radical, are Fusarium, e.g. *Fusarium avenaceum, Fusarium semitectum, Emericellopsis minima, Penicillium chrysogenum, Aspergillus ochraceus,* Cephalosporium sp. CMI 49137, Trichophyton, e.g. *Trichophyton mentagrophytes, Epidermophyton floccosum,* Streptomyces, e.g. *Streptomyces lavendulae.* The sediment of the microorganisms (which has been obtained in conventional manner by culturing) or the acylase extracts obtained from the cellular substances or purified acylases and compounds of the formula II are allowed to react with each other in aqueous solution. The acylase can be on a solid carrier, e.g. diatomaceous earth, silica gel, clay, aluminium oxide, kaolin, calcium phosphate, carboxymethyl cellulose, DEAE cellulose, TEAE cellulose, carboxymethyl dextran or polystyrene. If desired, it is possible to carry out the reaction continuously on the solid carrier. The pH of the solution and the reaction temperature are dependent on the nature of the acylases used. These reaction conditions can be inferred, for example, from the table on pp. 34–35 of the previously mentioned publication of Flynn. Upon termination of the deacylation (up to 96 hours) the cellular mass is optionally removed and the compounds of the formula I are isolated from the solution in the customary manner, for example by precipitation, evaporation (lyophilisation) or by chromatography. If desired, the solution which contains the compounds of the formula I can be used direct for the manufacture of the desired therapeutically active products, for example by treating them with a suitable acylating agent. The acylation can also be effected by a microbiological method, for example in analogous manner to that described in Belgian Patent No. 787 793.

The following Examples illustrate the invention.

EXAMPLE 1

A sterilised nutrient solution, is obtained by bulking 4 g of peptone, 4 g of meat extract and 4 g of sodium chloride to 200 ml with tap water (pH after the sterilisation: 6.5–7), is inoculated with *Escherichia coli* ATCC 9637 and the resultant suspension is shaken in an Erlenmeyer flask of 500 ml capacity for 18 hours at 26°C in a mechanical shaker at a speed of 250 rpm. Then 1 ml of the suspension is transferred to another Erlenmeyer flask of 500 ml capacity which contains 200 ml of the above nutrient solution and in addition 20 mg of phenylacetic acid and the suspension is again shaken at 26°C and 250 rpm in the menchanical shaker, this time for 24 hours. After centrifuging for 15 minutes at 0°C and 9000 rpm, the supernatant liquid is discarded and the sediment is suspended in 0.1 m phospahte buffer of pH 7. The suspension is centrifuged once more at 0°C for 15 minutes at 9000 rpm and the supernatant liquid is discarded. The sediment is suspended in phosphate buffer and the suspension is subsequently centrifuged.

500 mg of the moist cellular substance are suspended in a 50 ml capacity Erlenmeyer flask with 10 ml of phosphate buffer (pH 7) and 5 mg of 7-phenylacetamido-3-methoxy-ceph-3-em-4-carboxylic acid and the suspension is shaken for 15 hours in a water bath of 30°C, then centrifuged for 15 minutes at 9000 rpm. The aqueous solution contains the 7-amino-3-methoxy-ceph-3-em-4-carboxylic acid. In a thin layer chromatogram on cellulose it has the following Rf values: in the system n-butanol/glacial acetic acid/water (11-3-7) Rf = 0.51; in the system isopropanol/formic acid water (74:4:19) Rf = 0.33.

The identity of the compound was etablished by converting it into the phenyl-acetyl derivative: Whatman No. 1 filter paper discs (diameter 6 mm) are immersed in standard solution (containing 0.5 mg of 7-phenylacetamido-ceph-3em-carboxylic acid per ml of phosphate buffer) or in the above experimental solution, then fixed on pins and sprayed succesively with: (1) 10% pyridine in acetone, (2) 2% phenylacetylchloride in acetone, (3) 10% pyridine in acetone. They are subsequently laid on plates which are inoculated with *Bacillus subtilis* ATCC 6633 and incubated overnight at 37°C. An inhibitory zone of 22 mm in diameter is obtained in the standard solution and one of 12 mm in diameter in the phenylacetylated experimental solution. The experimental solution which has not been phenylacetylated has no inhibitory zone.

EXAMPLE 2

*Escherichia coli* ATCC 9637 is incubated at 26°C and 180 rpm in a sterilised nutrient solution consisting of 50 g of peptone, 50 g of meat extract, 50 g of sodium chloride and which is bulked to 500 ml with tap water. At an optical density of about 2.0 at 660 nm (measured in 10% dilution) the cells are centrifuged off, washed twice with 100 ml of 0.06 molar phosphate buffer (pH 7) and then disrupted with an X-press (Biox AB, Nacka, Sweden). The disrupted cells are extracted with phosphate buffer (pH 7) and the cell debris is then centrifuged off from the opalescent supernatant solution (crude extract). The crude extract is then fractionated by precipitation with solid ammonium sulphate. The fraction containing the acylase activity is precipitated by adding ammonium sulphate in an amount between 45% and 65% and is isolated by centrifuging. The solid is dissolved in 150 ml of 0.06 molar phosphate buffer (pH 7) and the solution is centrifuged for 15 hours 4°C in an ultracentrifuge (110,000 g). Afterwards acylase is concentrated in the sediment. The sediment is dissolved in 150 ml of phosphate buffer (pH 7) and filtered through Sephadex $^R$ G-200 (cross-linked polydextran gel of Pharmacia Fine Chemicals, Uppsala, with a fractionation range for proteins having a molecular weight of 5000 – 800,000). Fractions of 2.5 ml are collected. Fraction 22 contains the bulk of the acylase.

20 ml of this fraction are mixed with a solution of 100 mg 7-phenylacetamido-3-methoxy-ceph-3-em-4-carboxylic acid in 30 ml of water and the mixture is shaken for 15 hours in a water bath of 30°C. The solution is then lyophilised. The lyophilisate is taken up in 40 ml of a mixture of water and methanol (4:1) and the pH is adjusted to about 4.5 with 20% phosphoric acid. The precipitate is filtered off, washed with methanol and then with acetone and dried in a high vacuum. The 7-amino-3-methoxy-3-ceph-4-em-carboxylic acid is obtained in the form of the inner salt. In a thin layer chromatogram on silicagel in the system n-butanol/acetic acid/water (67:10:23) the compound has an Rf value of 0.16.

We claim:

1. A process for the manufacture of amino compounds of the formula I

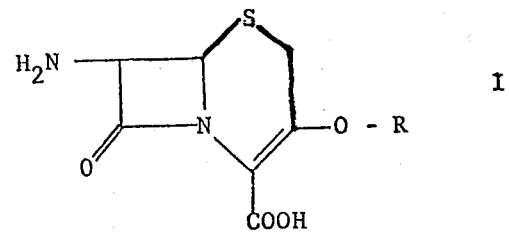

wherein R represents lower alkyl, wherein compounds of the formula II

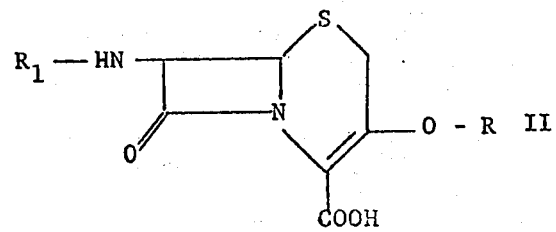

in which R has the meaning already assigned to it and $R_1$ represents the acyl radical of a carboxylic acid, are treated with microorganisms possessing acylase activity or with extracts containing acylase or with the acylases themselves, in aqueous medium, and the compounds of the formula I are isolated from the solution.

2. A process according to claim 1, wherein compounds of the formula II, in which R represents methoxy, are used as starting materials.

3. A process according to claim 1, wherein compounds of the formula II, in which $R_1$ represents phenylacetyl, are used as starting materials.

4. A process according to claim 3, which comprises the use of acylases of *Escherichia coli*.

* * * * *